United States Patent
Momma et al.

(10) Patent No.: US 10,874,851 B2
(45) Date of Patent: Dec. 29, 2020

(54) FLEXIBLE BAND TINE ARRAY, PARTICULARLY FOR AN IMPLANTABLE CARDIAC PACEMAKER

(71) Applicant: BIOTRONIK SE & Co. KG, Berlin (DE)

(72) Inventors: Carsten Momma, Rostock (DE); Wantjinarjo Suwito, West Linn, OR (US); Jeffrey A. von Arx, Lake Oswego, OR (US); Matthias Frotscher, Rostock (DE); Marco Bosselmann, Rostock (DE)

(73) Assignee: BIOTRONIK SE & Co. KG, Berlin (DE)

( * ) Notice: Subject to any disclaimer, the term of this patent is extended or adjusted under 35 U.S.C. 154(b) by 142 days.

(21) Appl. No.: 15/997,784

(22) Filed: Jun. 5, 2018

(65) Prior Publication Data
US 2018/0353754 A1 Dec. 13, 2018

Related U.S. Application Data

(60) Provisional application No. 62/516,689, filed on Jun. 8, 2017.

(51) Int. Cl.
| | |
|---|---|
| *A61N 1/05* | (2006.01) |
| *A61N 1/375* | (2006.01) |
| *A61B 5/00* | (2006.01) |
| *A61N 1/37* | (2006.01) |
| *A61N 1/372* | (2006.01) |

(52) U.S. Cl.
CPC .......... *A61N 1/0573* (2013.01); *A61B 5/6882* (2013.01); *A61N 1/3706* (2013.01); *A61N 1/3756* (2013.01); *A61N 1/37518* (2017.08); *A61B 5/686* (2013.01); *A61B 5/6852* (2013.01); *A61B 5/6862* (2013.01); *A61N 1/059* (2013.01); *A61N 1/37205* (2013.01); *A61N 1/37512* (2017.08)

(58) Field of Classification Search
CPC .. A61N 1/0573; A61N 1/3706; A61N 1/3756; A61N 1/37518; A61N 1/37205; A61N 1/059; A61N 1/37512; A61B 5/6882; A61B 5/6852; A61B 5/6862; A61B 5/686
See application file for complete search history.

(56) References Cited

U.S. PATENT DOCUMENTS

| | | | |
|---|---|---|---|
| 2003/0004537 A1* | 1/2003 | Boyle | A61F 2/013 606/200 |
| 2012/0172892 A1 | 7/2012 | Grubac et al. | |
| 2013/0085350 A1* | 4/2013 | Schugt | A61B 5/0031 600/302 |

(Continued)

*Primary Examiner* — Catherine M Voorhees
(74) *Attorney, Agent, or Firm* — Buchanan Ingersoll & Rooney PC

(57) ABSTRACT

An anchoring device for anchoring an implantable medical device to tissue of a patient, wherein the anchoring device comprises: an annular member, a plurality of elongated tines connected to the annular member and protruding from the annular member, wherein the annular member comprises at least one stretchable first section that is stretchable along a peripheral direction of the annular member. Further, the invention relates to an implantable medical device (e.g., an implantable cardiac pacemaker) comprising such an anchoring device.

18 Claims, 2 Drawing Sheets

(56) References Cited

U.S. PATENT DOCUMENTS

2015/0039069 A1\* 2/2015 Rys ................. A61N 1/362
                                              607/128
2016/0310726 A1\* 10/2016 Demmer ........... A61N 1/37211
2017/0209688 A1\* 7/2017 Drake ................ A61N 1/3688

\* cited by examiner

FLEXIBLE BAND TINE ARRAY, PARTICULARLY FOR AN IMPLANTABLE CARDIAC PACEMAKER

CROSS-REFERENCE TO RELATED APPLICATIONS

This patent application claims the benefit of U.S. Provisional Patent Application No. 62/516,689, filed on Jun. 8, 2017, which is hereby incorporated by reference in its entirety.

TECHNICAL FIELD

The present invention relates to an anchoring device for an implantable medical device, particularly for an implantable cardiac pacemaker, particularly an intra-cardiac pacing systems (IPS) or an epicardiac pacing system (EPS).

BACKGROUND

Intra-cardiac pacing systems (IPS) are small active implants completely implanted within a heart. These IPS comprise leadless pacemaker devices, which are small pacemakers anchored in the heart with anchoring devices. Usually these leadless pacemakers are VVI pacemakers (see NASPE Code), which are implanted in the ventricle of the heart able to sense right ventricular signals only, and pace in the right ventricle only. In recent times, so called VDD/DDD operations are getting more and more important, which means that at least signals from the right atrium shall be considered for the therapy. These intra-cardiac VDD pacing systems may have atrial extensions.

For the purpose of the patent application the term "EPS" is associated with "epicardiac pacing systems", which define pacing systems, which can be attached to the outside of the heart tissue. Such an EPS may be particularly applicable to left ventricular pacing. These EPS comprise leadless epicardial pacemakers, which are small pacemakers anchored to the outside of the heart. Further, cardiac leads with an so called passive fixation are also included in the term IPS or EPS.

Such an anchoring device usually comprises tines for anchoring the implantable medical device in the patient's tissue.

Individual tines have the flexibility of easy manufacturability (e.g., from flat ribbon Nitinol wire), and are relatively easy to configure to a number of tines (three, four or five) per IPS/EPS. However, they are more difficult to handle and assemble into an IPS/EPS header.

On the other hand, tine arrays with a fixed annular member (e.g., annular band) are easier to handle and assemble into an IPS/EPS header. However, any design change on the IPS/EPS header (e.g., a wider diameter IPS/EPS) may require design change on the tine array and the shape setting tools, which renders the manufacturing of the IPS/EPS more complex and expensive. Furthermore, tines with fixed band, as disclosed in U.S. Publication No. 2012/0172892, may translate stress through the band from one tine to another. Eventually, this may lead to long term reliability issues.

Thus, based on the above, a problem to be solved by the present invention is to provide an improved anchoring device and implantable medical device.

SUMMARY

At least this problem is solved by an anchoring device having the features of claim 1, as well as by an implantable medical device having the features of claim 11. Embodiments of these aspects of the present invention are stated in the corresponding sub claims and are described below.

According to claim 1, an anchoring device (also denoted as tine array) for anchoring an implantable medical device to human or animal tissue is disclosed, comprising: an annular member, a plurality of elongated tines connected to the annular member and protruding from the annular member, wherein, according to the present invention, the annular member comprises at least one stretchable first section that is stretchable along a peripheral direction of the annular member.

By providing at least one flexible first section on the connecting annular member, the above mentioned stresses are reduced. Further, one anchoring device may be used with a plurality of headers having different diameters. For example, one anchoring device with a certain (standard-diameter) annular member can be used for commonly known standard devices, and additionally, for example, for IPS/EPS with high capacity batteries, which usually have larger diameters. Because of the stretchability of the first section of the annular member, the diameter of the annular member accommodates to larger diameters. This simplifies the supply during production.

The anchoring device according to the present invention may be fabricated from a drawn tube, e.g., a Nitinol tube, that is laser cut to produce said tines protruding from an annular member. Particularly, a cutting process, as for example used in cutting vascular stents, may be employed. Particularly, see also below, the present invention is adding narrow meandering structures on the connecting annular member. The meandering structures allow for the band to expand or contract radially, just like in stents. Doing so, the tine array/anchoring device can be cut from a stock tube with a diameter that is near the intended finish diameter. It does not have to be cut from tubes with the final diameter. The still malleable and already cut anchoring device may then be shape set and heat treated to form an e.g. super-elastic Nitinol structure using shape setting tool(s). The result is a tine array, which is long lasting due to an independent strut action of each tine, and comprises less induced cross-stressing as well as great design flexibility when mating with other components in the IPS/EPS header. Further, the final diameter of the anchoring device's annular member/band can be readily changed to a certain extend. Finally, the annular member allows an interference fit with one of the IPS's or EPS's components for easier handling, assembling and less play.

According to an embodiment of the present invention, the at least one stretchable first section is elastically or super-elastically stretchable, particularly in the peripheral direction of the annular member, so that the at least one first section can be prolonged in the peripheral direction leading to a corresponding larger diameter of the annular member.

Further, according to an embodiment of the present invention, the annular member is a circular annular member. Further, according to an embodiment, the annular member is an (e.g., circular) band that comprises an (e.g., flat) rectangular cross section in a plane extending perpendicular to the peripheral direction of the annular member.

Further, according to an embodiment of the present invention, the at least one stretchable first section is connected to a neighboring second section of the annular member.

Further, according to an embodiment of the present invention, the annular member comprises a plurality of stretchable first sections, wherein each two neighboring first sections are connected to each other via one second section. Particularly, the at least one of the plurality of first section comprises a first end and an opposing second end, wherein each end is in turn connected to a neighboring second section of the annular member.

Further, according to an embodiment of the present invention, the stretchable first section in both aforementioned embodiments comprises a smaller effective stiffness than the neighboring second sections regarding stretching in the peripheral direction of the annular member. Particularly, according to this application, "effective stiffness" is an overall resistance to deformation of a structure that consists of non-homogenous members, material property or geometry wise, or combinations of both, under external loads.

Furthermore, according to a preferred embodiment of the present invention, the at least one stretchable first section in both aforementioned embodiments comprises a meandering shape. In an alternative embodiment, the stretchable section comprises a mesh, closed cell or helix structure, which is commonly known in the field of cardiac and peripheral stents, particularly self-expanding stents.

Particularly, the at least one stretchable first section in both aforementioned embodiments comprises a plurality of curved portions that are successively arranged along the peripheral direction and connected to one another so that the at least one first section extends along the peripheral direction from said first end to said second end as well as back and forth along an axial direction of the annular member, which axial direction particularly extends perpendicular to a radial direction of the annular member. Particularly, said axial direction coincides with a cylinder axis of the annular member.

Particularly, according to an embodiment of the present invention, the tines are integrally connected to the annular member of the anchoring device. Particularly, the tines protrude from the same circumferential edge of the annular member.

Further, according to an embodiment of the present invention, the at least one first section is arranged along the peripheral direction between two sections of the annular member, wherein each of the plurality of tines protrudes from each of said two sections of the annular member. Further, according to an embodiment of the present invention, each tine protrudes from an associated second section.

Particularly, in an embodiment of the present invention, the first sections are equidistantly spaced along the peripheral direction. Further, in an embodiment, the anchoring device comprises four first sections and four second sections as well as four tines, wherein each tine protrudes from an associated second section. Thus, in this embodiment, each tine is connected to its two neighboring tines via an (e.g., meandering) first section.

Further, according to an embodiment of the present invention, the tines are configured to move under the action of a restoring force from a first configuration in which the tines extend along said axial direction of the annular member to a second configuration in which each tine comprises a hook shape for engaging a patient's tissue.

In one embodiment, the restoring force of the stretched tine array locks the tine array onto one or more groves, recesses, notches, or indentations on the implantable medical device and holds it there via a compression fit. In this embodiment, the stretchable section not only relieves stress in the tines, but also holds the tines in place, simplifying assembly.

Further, according to an embodiment of the present invention, the annular member and/or said tines are formed out of a metal, particularly a superelastic metal, particularly a superelastic Nickel-Titanium-Alloy, particularly Nitinol (see also above).

A further aspect of the present invention relates to an implantable medical device comprising an anchoring device according to the present invention.

According to an embodiment of the implantable medical device, the implantable medical device is an implantable cardiac pacemaker, particularly an intra-cardiac pacing system.

Particularly, in an embodiment of the implantable medical device, the implantable medical device (e.g., pacemaker, particularly IPS) is configured to be implanted into a chamber of the patient's heart, particularly into the right or left ventricle or right atrium, particularly via a catheter. Further, EPS devices are configured for accessing the epicardium, i.e., the outer heart wall accessed through the pericardial space external the heart, for addressing sensing and stimulating of left sided chambers. The implantable medical implant (e.g., pacemaker, particularly IPS/EPS) may comprise a hermetically sealed housing. The housing may enclose a pulse generator for generating pacing pulses to the heart of the patient, and a battery for supplying energy to the pulse generator. Particularly, the anchoring device is mounted to the implantable medical device (e.g., pacemaker, particularly IPS/EPS) such that the tines protrude out of an outer diameter of the housing at a face side of the housing for fastening the medical device (e.g., pacemaker, particularly IPS/EPS) to tissue of the chamber/ventricle (when the tines are in the second configuration). The medical device (e.g., pacemaker, particularly IPS/EPS) may comprise at least two pacing electrodes, wherein one pacing electrode is provided on the face side of the housing of the medical device (e.g., pacemaker, particularly IPS/EPS) between the tines for applying the electrical stimulation to the heart. At least one additional second electrode is situated at or near the opposite end of the housing. The latter one can be configured as a return electrode, for example in the shape of a ring electrode.

According to another embodiment of the implantable medical device, the implantable medical device is an intra-cardiac lead with anchoring tines.

Particularly, in an embodiment of the implantable medical device, the intra-cardiac lead is configured to be attached to a chamber of the patient's heart, particularly into the right or left ventricle or right atrium. The intra-cardiac lead may comprise a lead body comprising an electrically insulating material, in which electrical conductor wires are embedded. The lead body may enclose a longitudinally extending lumen for guiding means like guide wires or mandrins, in order to steer the lead into the ventricle or atrium of the heart. Particularly, the anchoring device is mounted to the distal tip of the intra-cardiac lead such that the tines protrude from the distal end of the lead body for fastening the intra-cardiac lead to tissue of the chamber (when the tines are in the second configuration).

Further features, aspects, objects, advantages, and possible applications of the present invention will become apparent from a study of the exemplary embodiments and examples described below, in combination with the Figures, and the appended claims.

DESCRIPTION OF THE DRAWINGS

Other advantages and expedient features of the present invention follow from the following description of sample embodiments, which make reference to the Figures. The Figures are as follows.

DETAILED DESCRIPTION

Figure 1:
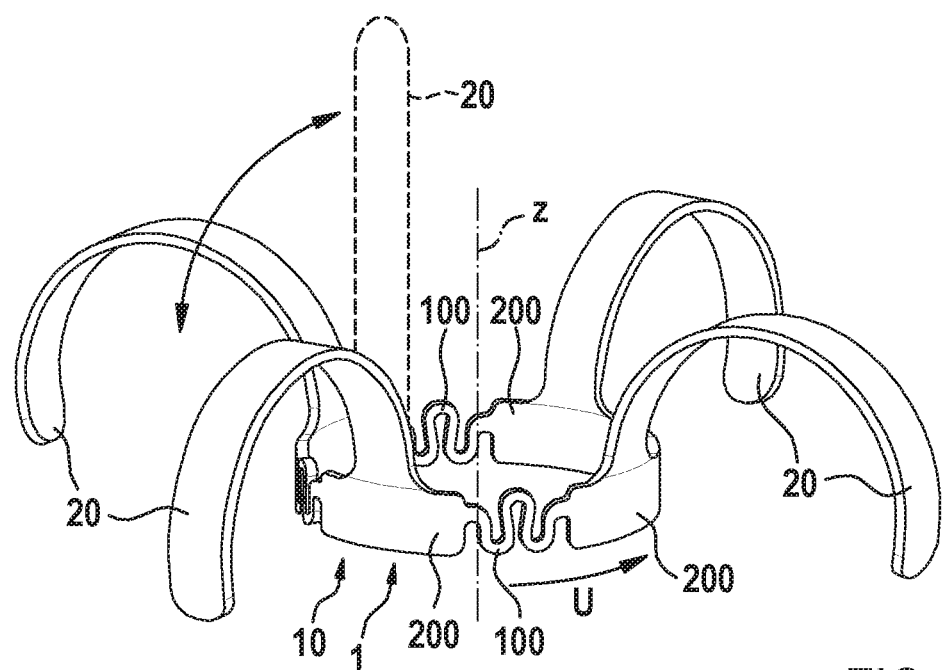
FIG. 1 shows a perspective view of an anchoring device according to the present invention.
Figure 2:
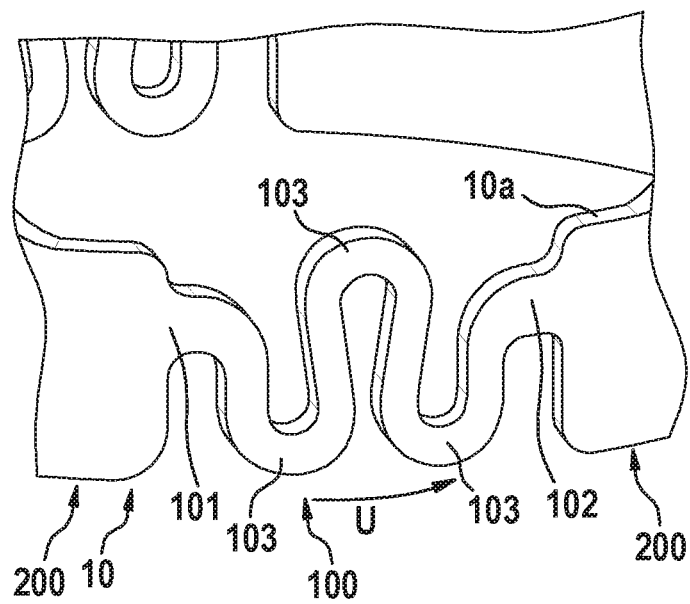
FIG. 2 shows a detail of FIG. 1.

FIGS. 1 and 2 show an embodiment of an anchoring device 1 according to the present invention for anchoring an implantable medical device 2 (depicted in FIG. 3) to tissue of a patient. The anchoring device 1, which is also denoted as a tine array, comprises an annular member 10 and a plurality of elongated tines 20 connected to the annular member 10 and protruding from the annular member 10. According to the present invention, the annular member 10 comprises at least one stretchable first section 100 that is stretchable along a peripheral direction U of the annular member 10.

Particularly, the annular member 10 is integrally connected to said tines 20, here to the same (e.g., upper) edge 10a of the annular member 10. Particularly, the annular member 10 and the tines 20 are formed out of a superelastic alloy comprising nickel and titanium, particularly Nitinol.

As shown in FIG. 1, the annular member 10, which is particularly formed as a circular band having (at least in sections) a rectangular cross section, comprises a plurality of stretchable first sections 100, here four first sections 100, wherein each two neighboring first sections 100, i.e., first sections 100 that are neighbors in the peripheral direction U of the annular member 10, are connected to each other via a second section 200.

As shown in FIGS. 1 and 2, the first sections 100 each comprise a meandering shape. Particularly, each first section 100 comprises a first end 101 and an opposing second end 102, wherein each end 101, 102 is connected to a neighboring second section 200 of the annular member 10. Further, particularly, the respective first section 100 comprises a plurality of curved portions 103 that are successively arranged along the peripheral direction U of the annular member and connected to one another so that the respective stretchable first section 100 extends along the peripheral direction U from its first end 101 to its second end 102 as well as back and forth along an axial direction z of the annular member 10. This allows stretching of the first sections 100 in the peripheral direction U, wherein the curvature of the curved portions 103 decreases leading to an elongation of the respective first section 100 in the peripheral direction U which in turn leads to an enlarged diameter of the annular member 10.

Further, each of the tines 20 protrudes from a second section 200 so that the individual tines are connected to each other via said meandering first sections 100.

Particularly, for the anchoring function, the tines 20 are configured to move under the action of a restoring force from a first configuration in which the tines 20 extend along an axial direction z of the annular member 10 (this first configuration is indicated for one tine 20 in FIG. 1 with a dashed line) to a second configuration in which each tine 20 comprises a hook shape for engaging a patient's tissue as shown in FIG. 1. Particularly, each hook-shaped tine 20 bends outwards so that the tines 20 form hooks in the second configuration that can be anchored in human or animal tissue at the implantation site (e.g., heart, particularly ventricle or atrium).

Figure 3:
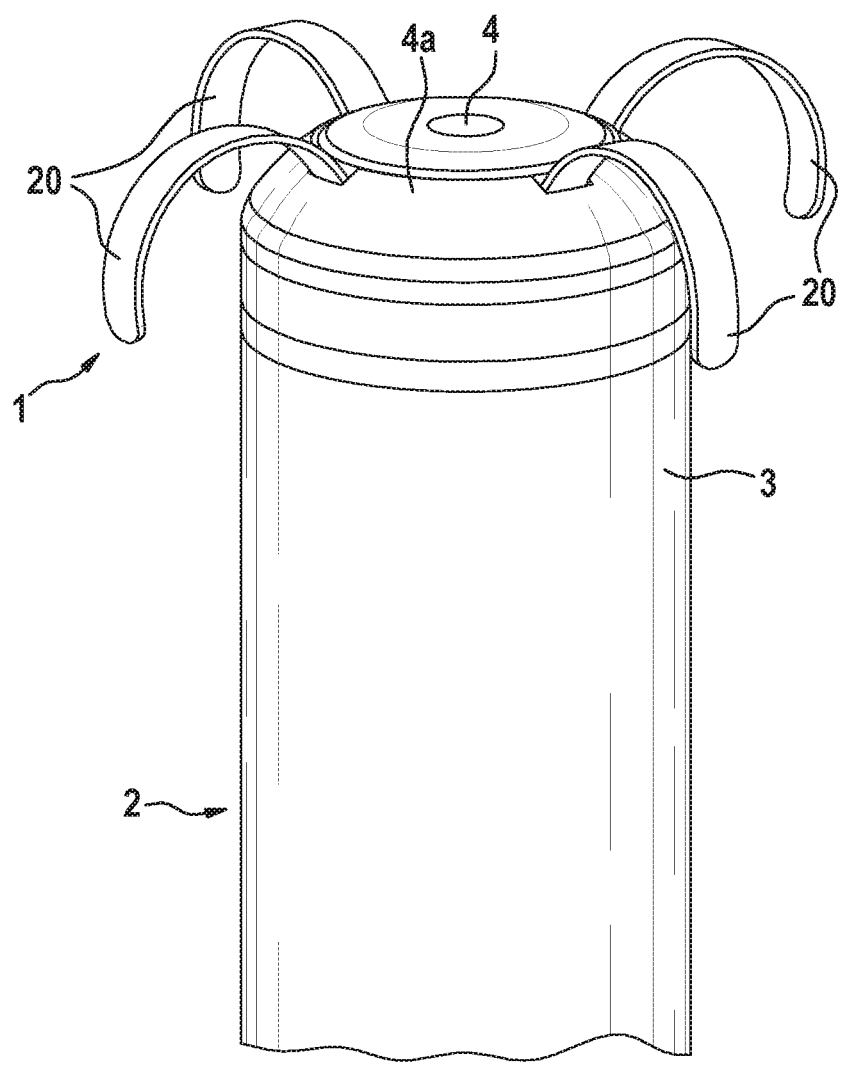
FIG. 3 shows an implantable medical device in the form of an intra-cardiac pacing system (IPS) comprising an anchoring device according to the present invention.

Further, FIG. 3 shows an implantable medical device 2 that comprises an anchoring device 1 according to the present invention. Here, as an example, said medical device 2 is an implantable cardiac pacemaker, particularly an intra-cardiac pacing system (IPS). However, in an alternative embodiment, the anchoring device 1 can also be implemented or mounted to a face side of an EPS or to a distal tip of an intra-cardiac lead for attaching the distal end to tissue of the chamber/ventricle, for example the trabecular network.

Such an IPS 2 is configured to be implanted into a ventricle or atrium of the patient's heart, particularly into the right or left ventricle or right atrium, particularly via a catheter. The IPS 2 particularly comprise a hermetically sealed housing 3 which particularly encloses a pulse generator for generating pacing pulses that are to be applied to the patient's heart via at least one pacing electrode 4 of the IPS 2 and a battery for supplying energy to the pulse generator. Particularly, the anchoring device 1 is mounted such in the IPS 2 that the tines 20 protrude out of the housing 3 of the IPS 2 at a face side 3a of the housing 3 for fastening the IPS 2 to tissue of the chamber/ventricle (when the tines 20 are in the second configuration), The pacing electrode 4 is particularly provided on the face side 4a of the housing 3 of the leadless pacemaker 2 between the tines 20 for applying said electrical stimulation to the heart of the patient. An additional second electrode, which works as a return electrode, is situated at or near the opposite end of the housing and can be configured as a ring electrode.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An anchoring device for anchoring an implantable medical device to tissue of a patient, the anchoring device comprising:

an annular member, a plurality of elongated tines connected to the annular member and protruding from the annular member, wherein the annular member comprises at least one stretchable first section that is stretchable along a peripheral direction of the annular member, the at least one stretchable first section is connected to a neighboring second section of the annular member, the at least one stretchable first section comprises a smaller effective stiffness than the neighboring second section, the at least one stretchable first section comprises a first end and an opposing second end, wherein each end is connected to a different neighboring second section of the annular member, and the at least one stretchable first section extends along the peripheral direction from the first end to the second end as well as back and forth along an axial direction of the annular member.

2. The anchoring device according to claim 1, wherein the annular member comprises a plurality of stretchable first sections, wherein each two neighboring first sections are connected to each other via one second section.

3. The anchoring device according to claim 2, wherein the at least one or the plurality of stretchable first sections comprise a first end and an opposing second end, wherein each end is connected to a different neighboring second section of the annular member.

4. The anchoring device according to claim 1, wherein each of the plurality of tines protrudes from each of said second sections of the annular member.

5. The anchoring device according to claim 1, wherein the tines are configured to move under the action of a restoring force from a first configuration in which the tines extend along an axial direction of the annular member to a second configuration in which each tine comprises a hook shape for engaging a patient's tissue.

6. The anchoring device according to claim 1, wherein the annular member and/or said tines are formed out of a superelastic metal.

7. An implantable medical device comprising an anchoring device according to claim 1.

8. The implantable medical device according to claim 7, wherein the implantable medical device is an implantable cardiac pacemaker.

9. The implantable medical device according to claim 8, wherein the implantable medical device is an intra-cardiac pacing system or epicardial pacing system.

10. An anchoring device for anchoring an implantable medical device to tissue of a patient, the anchoring device comprising:
an annular member,
a plurality of elongated tines connected to the annular member and protruding from the annular member, wherein
the annular member comprises at least one stretchable first section that is stretchable along a peripheral direction of the annular member,
the at least one stretchable first section is connected to a neighboring second section of the annular member,
the at least one stretchable first section comprises a smaller effective stiffness than the neighboring second section,
the at least one stretchable first section comprises a first end and an opposing second end, wherein each end is connected to a different neighboring second section of the annular member, and
the at least one stretchable first section comprises a plurality of curved portions that are successively arranged along the peripheral direction and connected to one another so that the at least one stretchable first section extends along the peripheral direction from said first end to said second end as well as back and forth along an axial direction of the annular member.

11. The anchoring device according to claim 10, wherein the annular member comprises a plurality of stretchable first sections, wherein each two neighboring first sections are connected to each other via one second section.

12. The anchoring device according to claim 11, wherein the at least one or the plurality of stretchable first sections comprise a first end and an opposing second end, wherein each end is connected to a different neighboring second section of the annular member.

13. The anchoring device according to claim 10, wherein each of the plurality of tines protrudes from each of said second sections of the annular member.

14. The anchoring device according to claim 10, wherein the tines are configured to move under the action of a restoring force from a first configuration in which the tines extend along an axial direction of the annular member to a second configuration in which each tine comprises a hook shape for engaging a patient's tissue.

15. The anchoring device according to claim 10, wherein the annular member and/or said tines are formed out of a superelastic metal.

16. An implantable medical device comprising an anchoring device according to claim 10.

17. The implantable medical device according to claim 16, wherein the implantable medical device is an implantable cardiac pacemaker.

18. The implantable medical device according to claim 16, wherein the implantable medical device is an intra-cardiac pacing system or epicardial pacing system.

* * * * *